United States Patent [19]

Matsuda et al.

[11] Patent Number: 5,650,540
[45] Date of Patent: Jul. 22, 1997

[54] METHOD OF PRODUCING AMIDE COMPOUND

[75] Inventors: Takashi Matsuda; Shinichi Sato; Noriyuki Koike, all of Gunma-ken, Japan

[73] Assignee: Shin-Etsu Chemical Co., Ltd., Tokyo, Japan

[21] Appl. No.: 550,234

[22] Filed: Oct. 30, 1995

[30] Foreign Application Priority Data

Oct. 31, 1994 [JP] Japan .................................. 6-288618

[51] Int. Cl.$^6$ .................................................. C07C 231/02
[52] U.S. Cl. ........................ 564/143; 544/390; 546/245; 564/142; 564/209; 564/210; 564/211; 568/410
[58] Field of Search ........................ 564/142, 143, 564/209, 210, 211; 568/410

[56] References Cited

U.S. PATENT DOCUMENTS

| 2,824,884 | 2/1958 | Barnhart et al. ................. 260/404 |
| 3,250,808 | 5/1966 | Moore, Jr. et al. ................ 260/535 |

FOREIGN PATENT DOCUMENTS

| 0 265 052 | 4/1988 | European Pat. Off. . |
| 61-036101 | 2/1986 | Japan . |
| 1067788 | 5/1967 | United Kingdom . |

*Primary Examiner*—Shailendra Kumar
*Attorney, Agent, or Firm*—Millen, White, Zelano, & Branigan, P.C.

[57] ABSTRACT

Provided is a method of producing a highly pure amide compound in a high yield, wherein a silazane compound and/or a silane compound having at least one silicone-nitrogen bond are added to a reaction mixture obtained by reacting an acylfluoride group-containing compound with an amino compound, wherein the amide compound is present together with hydrogen fluroide and/or the amine hydrofluoride, thereby removing the hydrogen fluoride and/or the amine hydrofluoride from the reaction mixture.

11 Claims, No Drawings

METHOD OF PRODUCING AMIDE COMPOUND

FIELD OF THE INVENTION

The present invention relates to a method of producing an amide compound and, more particularly, to a method of obtaining a highly pure amide compound in a high yield by giving a simple treatment to a reaction mixture prepared by the reaction of an acylfluoride group-containing compound with an amino compound.

BACKGROUND OF THE INVENTION

As a method of producing an amide compound from an acylfluoride group-containing compound, the direct reaction of the acylfluoride group-containing compound with an amino compound has so far been adopted. These compounds are known to react stoichiometrically with each other.

In this reaction, hydrogen fluoride is produced as a by-product. If the amino compound is used in excess of its stoichiometric amount, the hydrogen fluoride produced combines with the excess amino compound to form an amine salt.

On other hand, there is known a case in which an amino compound as acid acceptor is further added to the reaction system. In such a case, an amine salt is also formed between the hydrogen fluoride and the amino compound added.

In order to isolate an intended amide compound by removing the salt(s) formed by hydrogen fluoride and amino compound(s) (hereinafter called amine hydrofluoride(s)) from the reaction system, it is prevalent to adopt an after-treatment with water.

However, it has sometimes occurred that amide compounds produced had poor separability from water. Under such a situation, the conventional direct reaction method has problems such that it requires considerable hours and many separation steps to obtain an intended amide compound in a highly pure form, a large quantity of amine hydrofluorides remain in the products obtained because of incomplete purification, reduction in yield is unavoidable, and so on.

In another case, it is possible to isolate the intended amide compounds by distillation. Even if it is so, in so far as the removal of amine hydrofluorides is incomplete in the step prior to distillation, the distillation step suffers troubles such that amine hydrofluorides contaminate distilled fractions through their sublimation during the distilling operation and occasionally deposit in the cooling zone of a distilling column to clog the distilling column.

SUMMARY OF THE INVENTION

As a result of our intensive studies on the method of obtaining an intended amide compound of high purity in a high yield by a simple operation from a reaction mixture produced from an acylfluoride group-containing compound and an amino compound, it has been found that the conventional aftersteps can be simplified by the addition of a silazane compound or/and a silane compound having at least one Si—N bond to the foregoing reaction mixture since the amine hydrofluoride in the reaction mixture can be converted into the fluorosilane compound and the amino compound through the reaction with the compound added to result in the disappearance thereof and the hydrogen fluoride in the reaction mixture also causes the reaction with the compound added to produce the fluorosilane compound and the amino compound, thereby achieving the present invention.

Therefore, an object of the present invention is to provide a method of producing an amide compound of high purity in a high yield by simple operations which comprises a step of isolating the amide compound from a reaction mixture obtained by reacting an acylfluoride group-containing compound with an amino compound.

The aforementioned object of the present invention is attained by a method of producing an amide compound which comprises a step of adding at least one Si—N bond-containing compound selected from the group consisting of silazane compounds and silane compounds having at least one Si—N bond to a reaction mixture obtained by reacting an acylfluoride group-containing compound with an amino compound, wherein the amide compound is present together with hydrogen fluoride and/or the amine hydrofluoride, thereby removing the hydrogen fluoride and/or the amine hydrofluoride from the reaction mixture.

In accordance with the present method, hydrogen fluoride and amine hydrofluorides present as by-products in the reaction system can be simply disposed of in a short time, and an intended amide compound can be obtained in a high yield and high purity.

DETAILED DESCRIPTION OF THE INVENTION

In the first place, the reaction of an acylfluoride group-containing compound with an amino compound is carried out in a conventional manner, wherein an appropriate solvent may be present or not, to produce a reaction mixture. This reaction mixture comprises an intended amide compound and hydrogen fluoride as a by-product and/or the amine hydrofluoride formed by the reaction of the hydrogen fluoride with the amino compound used in excess, which are produced, e.g., according to the following reaction formulae (1) and (2):

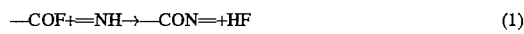  (1)

  (2)

In a case where a tertiary amino compound which can produce no amide compound because of its incapability to react with an acylfluoride group is added as an acid acceptor to the reaction system, the tertiary amino compound reacts with the hydrogen fluoride present therein as a by-product to result in the formation of another amine hydrofluoride.

The expression "acylfluoride group-containing compound" used in the present invention is intended to include compounds containing one or a plurality of acylfluoride groups per molecule. Suitable examples of such a compound include the compounds represented by the following general formulae, which are not to be considered as limiting on the scope of the invention:

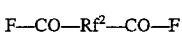

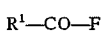

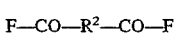

In the above formulae, $Rf^1$ represents a monovalent perfluoroalkyl group or a monovalent perfluoroalkyl ether group which has at least one oxygen atom forming an ether linkage, and $Rf^2$ represents a divalent perfluoroalkylene group or a divalent perfluoroalkylene ether group which has at least one oxygen atom forming an ether linkage.

$R^1$ represents a monovalent hydrocarbon group having 1 to 20 carbon atoms, preferably 1 to 10 carbon atoms, including alkyl groups such as a methyl group, an ethyl group, a propyl group, an isopropyl group, a butyl group, an isobutyl group, a tert-butyl group, a pentyl group, a neopentyl group, a hexyl group, a cyclohexyl group, a heptyl group, an octyl group, a nonyl group, a decyl group, an undecyl group, a dodecyl group, a tridecyl group, a pentadecyl group, a heptadecyl group, etc. and aryl groups such as a phenyl group, a tolyl group, a xylyl group, a naphthyl group, a biphenyl group, a trifluoromethylphenyl group, etc.

$Rf^2$ represents a divalent hydrocarbon group having 1 to 20 carbon atoms, preferably 1 to 10 carbon atoms, including alkylene groups such as a methylene group, an ethylene group, a propylene group, a tetramethylene group, a hexamethylene group, a methylethylene group, a methylpropylene group, an octamethylene group, etc., arylene groups such as a phenylene group, a tolylene group, a xylylene group, a naphthylene group, a biphenylene group, a trifluoromethylphenylene group, etc. and combinations of alkylene and arylene groups as cited above.

As for the groups represented by $Rf^1$ and $Rf^2$ respectively, the following are specific examples thereof:

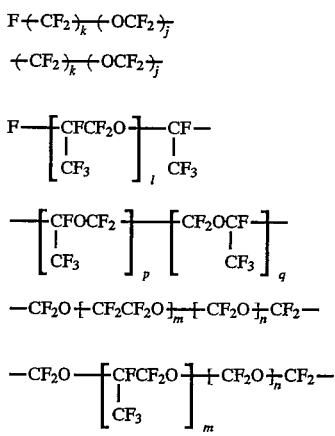

wherein j is 0 or 1; k is an integer ranging from 1 to 10; l is an integer ranging from 1 to 80, preferably from 1 to 50, more preferably from 1 to 20, and most preferably from 1 to 10; m is an integer ranging from 1 to 20, n is an integer ranging from 1 to 10; and p and q are each an integer of no smaller than 1, provided that the sum of p and q is an integer ranging from 2 to 80, preferably from 3 to 50, and the integer suitable for each of them ranges from 1 to 15.

With respect to acylfluoride group-containing compounds in which two or more of acylfluoride groups are present, some of these groups may be replaced by alkyl ester groups such as methyl ester groups, ethyl ester groups or the like so long as at least one acylfluoride group per one molecule remains unchanged.

Specific examples of an acylfluoride group-containing compound which can be employed in the present invention are illustrated below:

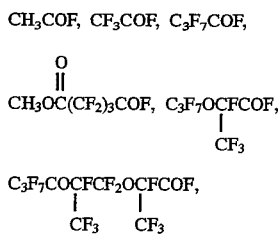

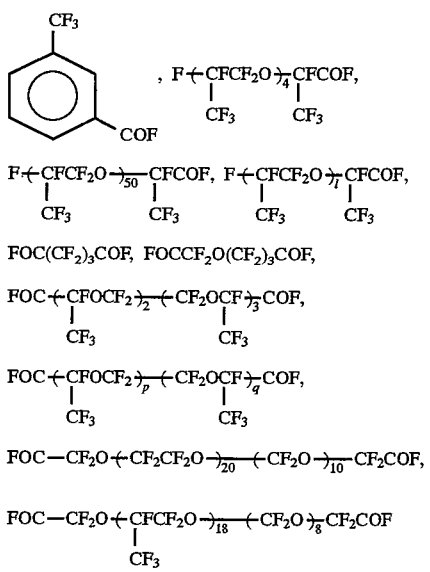

The letters l, p and q in the above structural formulae have the same meanings as those used respectively in the description of the structural formulae representing $Rf^1$ and $Rf^2$.

As for the amino compound which can react with the aforementioned acylfluoride group-containing compounds to produce amide compounds, it can be chosen from the group consisting of ammonia, primary amino group-containing compounds and secondary amino group-containing compounds.

To the foregoing reaction mixture, an amino compound as an acid acceptor, which may be similar to or different from the amino compounds described above as a starting material, can be further added in order that the hydrogen fluoride present in the reaction mixture may be converted into a salt by the reaction therewith.

Specifically, an amino compound used as an acid acceptor can be chosen from the group consisting of ammonia, primary amino group-containing compounds, secondary amino group-containing compounds and tertiary amino group-containing compounds.

As for the primary amino group-containing compounds which can be used, examples thereof are monoalkylamines such as methylamine, ethylamine, propylamine, isopropylamine, butylamine, isobutylamine, tert-butylamine, hexylamine, octylamine, decylamine, cyclohexylamine, etc., monoalkenylamines such as allylamine, propenylamine, isopropenylamine, butenylamine, etc., monoarylamines such as aniline, etc., 2-aminopyridine, and so on.

As for the secondary amino group-containing compounds which can be used, examples thereof are dialkylamines such as dimethylamine, dibutylamine, methylethylamine, dilbutylamine, etc., piperidine, piperazine, N-methylallylamine, diphenylamine, and so on.

As for the tertiary amino group-containing compounds which can be used, examples thereof are trialkylamines such as triethylamine, tributylamine, etc.

In a case where an amino compound as cited above is intended for an acid acceptor as well as a starting material, it can suffice for the intention to use the amino compound in excess of a stoichiometric amount required for the reaction with an acylfluoride group-containing compound as cited above, provided that the same shall not apply to the compounds having tertiary amino groups alone. This is because the compounds of that type cannot react with the aforementioned acylfluoride group-containing compounds as the other starting material although they can react with hydrogen fluoride to form amine hydrofluorides, and so they are often used as acid acceptor.

In the foregoing reaction, although it is not always required to use a solvent, solvents having no influence upon the reactions in the present invention, e.g., aprotic polar solvents such as toluene, hexane, tetrahydrofuran, glyme, etc., or fluorine-containing solvents, may be used, if desired.

In the next place, the reaction mixture prepared in the above-described manner is admixed with a silazane compound or a silane compound in which at least one silicon-nitrogen bond is present for the purpose of removing the hydrogen fluoride and/or amine hydrofluorides contained therein. As a result of the admixture, fluorosilane compounds and amino compounds are newly produced, but they can be easily excluded or separated by a stripping or distilling operation. Thus, the present method not only renders the conventional after-treatment with water unnecessary, thereby simplifying the aftersteps, but also enables substantial reductions of contents of impurities, especially a content of hydrogen fluoride, in the final product as an intended amide compound.

The reactions relating to the present method are described in detail below.

When the foregoing reaction mixture is admixed with a silazane compound or a compound having at least one silicon-nitrogen bond, the amine hydrofluoride present therein reacts with the compound added to produce a fluorosilane compound and amino compounds, and the compound added reacts also with the hydrogen fluoride present therein to yield similar products, that is, a fluorosilane compound and an amino compound.

Representative reactions which proceed therein are illustrated with the following reaction formulae:

a) Reaction of Amine hydrofluoride with Compound having One Si—N Bond

$$HF \cdot NR^{30}{}_3 + R^{32}{}_3SiNR^{31}{}_2 \rightarrow R^{32}{}_3SiF + NR^{30}{}_3 + HNR^{31}{}_2 \quad (3)$$

b) Reaction of Amine hydrofluoride with Disilazane $$HF \cdot NR^{30}{}_3 + R^{32}{}_3SiNHSiR^{32}{}_3 \rightarrow R^{32}{}_3SiF + NR^{30}{}_3 + R^{32}{}_3SiNH_2 \quad (4)$$

$$HF \cdot NR^{30}{}_3 + R^{32}{}_3SiNH_2 \rightarrow R^{32}{}_3SiF + NR^{30}{}_3 + NH_3 \quad (5)$$

In the above formulae (3), (4) and (5), each $R^{30}$, each $R^{31}$ and each $R^{32}$ individually represent a hydrogen atom or a monovalent hydrocarbon group. These reactions can proceed quickly and almost quantitatively. The fluorosilane compounds produced in those reaction processes are relatively stable compounds. For instance, trimethylfluorosilane, which corresponds to the compound in which all the three substituents attached to Si atom, or three $R^{32}$ groups, are methyl groups, has a boiling point of about 17° C. under the atmospheric pressure, and so it can be separated and removed with ease. Thus, almost complete removal of hydrogen fluoride and amine hydrofluorides from the reaction mixture becomes possible.

The silane compounds which can be used in the present invention are represented by the formula (I) illustrated below:

wherein at least one, preferably one, two or three, of the substituents $R^1$ to $R^4$ is a group represented by the formula (II) or (III);

and the other substituents, which are not the groups represented by the above formula (II) or (III), are the same or different, and each substituent is a hydrogen atom or an unsubstituted or substituted monovalent hydrocarbon group containing 1 to 8 carbon atoms, preferably 1 to 6 carbon atoms, particularly 1 to 4 carbon atoms; and wherein $R^5$ and $R^6$ are the same or different, and each substituent is a hydrogen atom or an unsubstituted or substituted monovalent hydrocarbon group containing 1 to 8 carbon atoms, preferably 1 to 6 carbon atoms, particularly 1 to 4 carbon atoms, and optionally one or more of a hetero atom, such as nitrogen, oxygen, etc., in the carbon chain; and $R^7$ is a substituted or unsubstituted divalent hydrocarbon group containing 2 to 8 carbon atoms and optionally one or more of a hetero atom, such as nitrogen, oxygen, etc., in the carbon chain.

As examples of an unsubstituted or substituted monovalent hydrocarbon group suitable for the substituents $R^1$ to $R^4$ except those represented by the foregoing formula (II) or (III), and for the substituents $R^5$ and $R^6$, mention may be made of alkyl groups, such as methyl, ethyl, propyl, isopropyl, butyl, isobutyl, tert-butyl, pentyl, neopentyl, hexyl, heptyl, octyl and like groups; cycloalkyl groups, such as cyclopentyl, cyclohexyl, cycloheptyl and like groups; alkenyl groups, such as vinyl, allyl, propenyl, isopropenyl, butenyl, isobutenyl, hexenyl, cyclohexenyl and like groups; aryl groups, such as phenyl, tolyl, xylyl and like groups; aralkyl groups, such as benzyl, phenylethyl, phenylpropyl and like groups; and the groups formed by replacing at least part of the hydrogen atoms of the groups as cited above with halogen atom(s), such as fluorine, bromine, chlorine, etc., including chloromethyl, 2-bromoethyl, 3-chloropropyl, 3,3,3-trifluoropropyl, 3,3,4,4,5,5,6,6,6-nonafluorohexyl and the like.

As examples of an unsubstituted or substituted divalent hydrocarbon group suitable for the substituent $R^7$, mention may be made of alkylene groups, such as ethylene, propylene, tetramethylene, pentamethylene, hexamethylene, methylethylene, methylpropylene and like groups; arylene groups, such as phenylene, tolylene, xylylene and like groups; and alkenylene groups, such as —CH=CH—CH=CH—.

With respect to the hetero atom-containing monovalent hydrocarbon group as the substituent $R^5$ or $R^6$, the following are specific examples thereof:

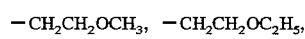

$—CH_2CH_2OCH_3, \quad —CH_2CH_2OC_2H_5,$

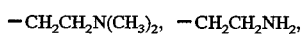
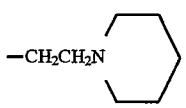

With respect to the hetero atom-containing divalent hydrocarbon group as the substituent $R^7$, the following are specific examples thereof:

—N=CH—N=CH—, —NH—CH=CH—NH—, —CH=CH—N=CH—, —CH$_2$CH$_2$OCH$_2$CH$_2$—, and —CH$_2$CH$_2$NHCH$_2$CH$_2$—.

Specific examples of a silane compound represented by the foregoing formula (I) are illustrated below, but it should be understood that these examples are not to be construed as limiting the scope of the invention in any way. Additionally, Me, Et and Ph in the following structural formulae stand for a methyl group, an ethyl group and a phenyl group, respectively.

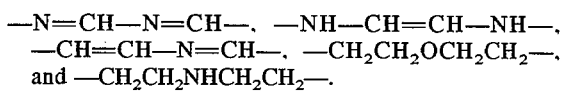
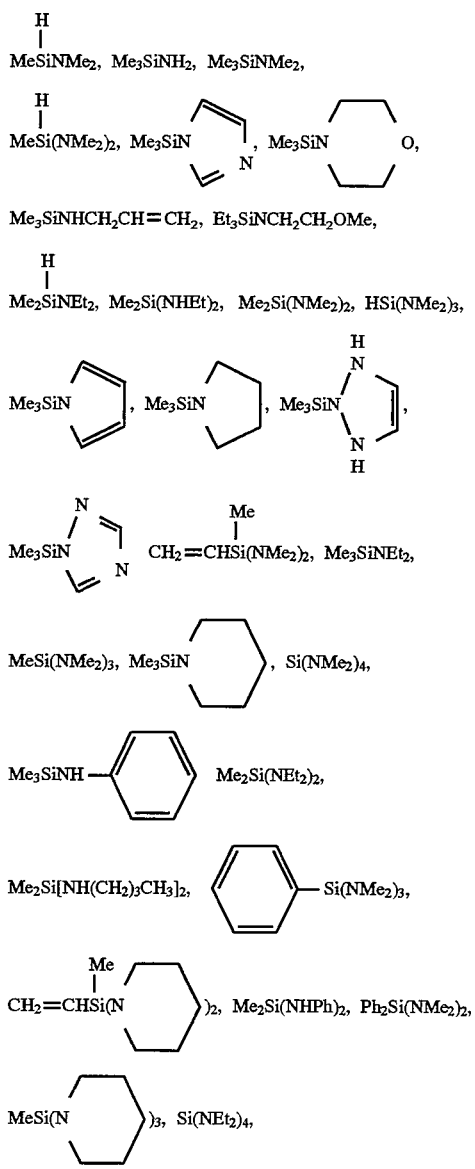

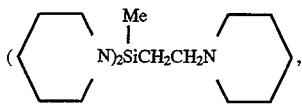
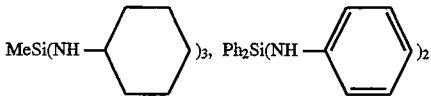

As examples of a silazane compound which can be used, mention may be made of disilazanes such as a tetraorganodisilazane, a heptaorganodisilazane, a hexaorganodisilazane, etc.; trisilazanes such as a hexaorganocyclotrisilazane, etc.; and tetrasilazanes such as an octaorgano-cyclotetrasilazane, etc. In these silazane compounds, hydrogen atoms attached to the silicon atoms can be partly replaced with unsubstituted or substituted monovalent hydrocarbon groups containing 1 to 8 carbon atoms, examples of which include those cited above with respect to the substituents $R^1$ to $R^4$.

Specific examples of such silazane compounds include 1,1,3,3-tetramethyldisilazane, 1,3-bis(chloromethyl)-1,1,3,3-tetramethyldisilazane, 1,1,1,3,3,3-hexamethyldisilazane, heptamethyldisilazane, 1,3-divinyl-1,1,3,3-tetramethyldisilazane, 1,3-bis(3,3,3-trifluoropropyl) tetramethyldisilazane, 1,3-dibutyl-1,1,3,3-tetramethyldisilazane, 1,3-diethyl-1,1,3,3-tetramethyldisilazane, hexamethylcyclotrisilazane, octamethylcyclotetrasilazane and 2,4,6-trimethyl-2,4,6-trivinylcyclo-trisilazane.

The silane or silazane compound as described above is used in a quantity such that the number of Si—N bonds present therein may be 1.0 to 10.0 times, preferably 1.0 to 5.0 times, as many as the number of the acylfluoride groups present in the amount of the acylfluoride group-containing compound used. When the quantity of the silane or silazane compound used is smaller than the aforementioned lower limit, the disposal of amine hydrofluorides becomes incomplete; while the use of the silane or silazane compound in excess of the foregoing upper limit is wasteful although it has no adverse influence upon the reaction system. A suitable temperature for the reaction is generally in the range of 0° C. to 80° C.

The present invention will now be illustrated in more detail by means of specific examples but it will be understood that it is not to be construed as being limited by these examples in any way.

EXAMPLE 1

In a 100 ml three-neck flask equipped with a Dimroth condenser, a thermometer, a dropping funnel and a stirrer was placed 8.8 g (120 millimole) of n-butylamine. An acylfluoride compound represented by the following formula (i) in an amount of 24.9 g (50 millimole) was dropped into the n-butylamine from the dropping funnel over a period of about 30 minutes while stirring.

During the dropping, the temperature inside the flask rose to 48° C. from 23° C., and the interior of the flask became turbid in white color due to the production of an amine hydrofluoride. After the conclusion of the dropping, the temperature inside the flask was cooled to 25° C. Then, diethylaminotrimethylsilane in the amount of 10.9 g (75 millimole) was dropped into the reaction mixture from the dropping funnel over a period of abut 5 minutes. As the dropping went on, the white turbidity inside the flask was gradually lightened. In 10 minutes after the conclusion of the dropping, the contents in the flask became transparent in light yellow color.

At this point of time, although the temperature inside the flask was 26° C., a refluxing liquid was present in the Dimroth condenser. Therefore, a trap cooled down to −40° C. was attached to the exit of the Dimroth condenser, and then the cooling of the Dimroth condenser was stopped. The thus trapped liquid was colorless and transparent. This liquid was dissolved in carbon tetrachloride, and analyzed by the measurement of $^1$H-NMR and $^{19}$F-NMR spectra. As the $^1$H-NMR spectrum (TMS standard) measured had a peak at δ=0.255 ppm (d) to be assigned for $CH_3$—Si and the $^{19}$F-NMR spectrum ($CF_3COOH$ standard) measured had a peak at δ=−80.20 ppm (m) to be assigned for Si—F, the liquid was confirmed to be trimethylfluorosilane.

Then, the liquid inside the flask was distilled, and thereby was obtained 26.2 g of a colorless transparent liquid having a boiling point of 107° C./15 mmHg (yield: 95%). The thus obtained liquid was analyzed by the measurement of $^1$H-NMR, $^{19}$F-NMR and IR spectra. As a result thereof, the liquid was confirmed to be an amide compound represented by the formula (ii) illustrated below.

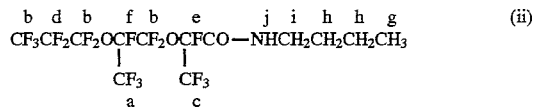

$^1$H-NMR (TMS standard) g: δ=0.77~1.10 (m, 3H); h: δ=1.10~1.83 (m, 4H); i: δ=3.10~3.57 (m, 2H); j: δ=6.73~7.17 (br, 1H).

$^{19}$F-NMR ($CF_3COOH$ standard) a: δ=−3.69 ppm; b: δ=−5.12 ppm; c: δ=−6.17 ppm; d: δ=−52.76 ppm; e: δ=−55.57 ppm; f: δ=−67.82 ppm.

IR $v_{+sc\ N-H}$:3330 cm$^{-1}$; $v_{+sc\ C-O}$:1702 cm$^{-1}$; $δ_{+sc\ N-H}$:1545 cm$^{-1}$; $v_{+sc\ C-F}$:1100~1300 cm$^{-1}$.

Further, F$^-$ contamination of the amide compound obtained was determined by ion chromatography. Thus, the F$^-$ content was found to be 3.7 ppm.

EXAMPLE 2

The synthesis of the amide compound represented by the foregoing formula (ii) was carried out in the same manner as in Example 1, except that hexamethyldisilazane in the amount of 12.1 g (75 millimole) was used in place of diethylaminotrimethylsilane. Therein, the production of trimethylfluorosilane was confirmed, and 26.3 g (yield: 95%) of the intended amide compound was obtained.

Further, F$^-$ contamination of the amide compound obtained was determined by ion chromatography. Thus, the F$^-$ content was found to be 6.0 ppm.

EXAMPLE 3

The synthesis of the amide compound represented by the foregoing formula (ii) was carried out in the same manner as in Example 1, except that hexamethylcyclotrisilazane in the amount of 7.4 g (34 millimole) was used in place of diethylaminotrimethylsilane. The colorless, transparent fraction trapped in the course of the synthesis was analyzed by the measurement of $^1$H-NMR and $^{19}$F-NMR spectra. As the $^1$H-NMR spectrum (TMS standard) measured had a peak at δ=0.34 ppm (t) to be assigned for $CH_3$—Si and the $^{19}$F-NMR spectrum ($CF_3COOH$ standard) measured had a peak at δ=−53.95 ppm (m) to be assigned for Si—F, the fraction was confirmed to be dimethyldifluorosilane. As a result of this synthesis, 26.8 g (yield: 97%) of the intended amide compound was obtained. Further, F$^-$ contamination of the amide compound obtained was determined by ion chromatography. Thus, the F$^-$ content was found to be 3.4 ppm.

EXAMPLE 4

Another amide compound was prepared in the same manner as in Example 1, except that 15.5 g (120 millimole) of di-n-butylamine was used in place of n-butylamine and 5.5 g (38 millimole) of bis(dimethylamino)dimethylsilane was used in place of diethylaminotrimethylsilane. Therein, the production of dimethyldifluorosilane was confirmed. Then, the liquid inside the flask was distilled, and thereby was obtained 30.1 g of a colorless transparent liquid having a boiling point of 118° C./20 mmHg (yield: 96%). The thus obtained liquid was analyzed by the measurement of $^1$H-NMR, $^{19}$F-NMR and IR spectra. As a result thereof, the liquid was confirmed to be an amide compound represented by the formula (iii) illustrated below.

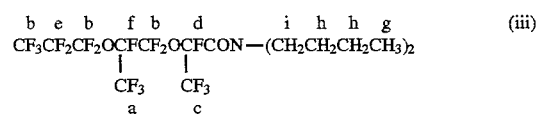

$^1$H-NMR (TMS standard) g: δ=0.83~1.17 (m, 6H); h: δ=1.17~1.98 (m, 8H); i: δ=3.04~3.70 (m, 4H).

$^{19}$F-NMR ($CF_3COOH$ standard) a: δ=−3.66 ppm; b: δ=−5.10 ppm; c: δ=−5.21 ppm; d: δ=−46.97 ppm; e: δ=−52.74 ppm; f: δ=−67.38 ppm.

IR $v_{+sc\ C-O}$:1690 cm$^{-1}$; $v_{+sc\ C-F}$:1100~1300 cm$^{-1}$.

Further, F$^-$ continuation of the amide compound obtained was determined by ion chromatography. Thus, the F$^-$ content was found to be 3.8 ppm.

EXAMPLE 5

Still another amide compound was prepared in the same manner as in Example 1, except that 5.6 g (60 millimole) of aniline was used in place of n-butylamine, 6.0 g (59 millimile) of triethylamine was further added, and 12.1 g (75 millimole) of hexamethyldisilazane was used in place of diethylaminotrimethylsilane. Therein, the production of trimethylfluorosilane was confirmed. Then, the liquid inside the flask was distilled, and thereby was obtained 26.7 g of a colorless transparent liquid having a boiling point of 91° C./2 mmHg (yield: 93%). The thus obtained liquid was analyzed by the measurement of $^1$H-NMR, $^{19}$F-NMR and IR spectra. As a result thereof, the liquid was confirmed to be an amide compound represented by the formula (iv) illustrated below. Additionally, Ph in the formula stands for a phenyl group.

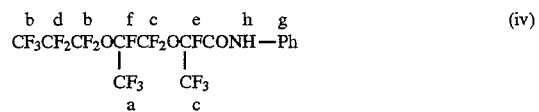

$^1$H-NMR (TMS standard) g: δ=7.02~7.53 (m, 5H); h: δ=8.16~8.46 (br, 1H).

$^{19}$F-NMR ($CF_3COOH$ standard) a: δ=−3.70 ppm; b: δ=−5.11 ppm; c: δ=−5.89 ppm; d: δ=−52.78 ppm; e: δ=−54.83 ppm; f: δ=−67.87 ppm.

IR $\nu_{+sc\ N-H}$:3320 cm$^{-1}$; $\nu_{+sc\ C-O}$:1710 cm$^{-1}$; $\delta_{+sc\ N-H}$:1540 cm$^{-1}$; $\nu_{+sc\ C-F}$:1100~1300 cm$^{-1}$.

Further, F$^-$ contamination of the amide compound obtained was determined by ion chromatography. Thus, the F$^-$ content was found to be 3.8 ppm.

EXAMPLE 6

In a 100 ml three-neck flask equipped with a Dimroth condenser, a thermometer, a dropping funnel and a stirrer was placed 55.0 g of an acylfluoride compound represented by the following formula (v), wherein the mean of the sum of a and b was 16. Into the acylfluoride compound, di-n-butylamine in the amount of 12.4 g (96 millimole) was dropped from the dropping funnel over a period of about 10 minutes while stirring.

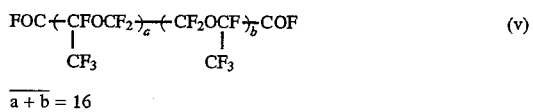

$\overline{a+b} = 16$

During the dropping, the temperature inside the flask rose to 50° C. from 22° C., and the interior of the flask became turbid in white color due to the production of an amine hydrofluoride. After the conclusion of the dropping, the temperature inside the flask was cooled to 27° C., and then a trap cooled down to –40° C. was attached to the exit of the Dimroth condenser. Then, hexamethyldisilazane in the amount of 10.9 g (68 millimole) was dropped into the reaction mixture from the dropping funnel over a period of about 5 minutes. In 15 minutes after the conclusion of the dropping, the contents in the flask became transparent in light yellow color. At this point of time, the temperature inside the flask was 27° C.

The trapped liquid was analyzed, and confirmed to be trimethylfluorosilane. Then, the liquid inside the flask was subjected to a one-hour stripping operation under a condition of 150° C./5 mmHg while bubbling with nitrogen gas. Thus, 58.2 g of a colorless transparent liquid was obtained (yield: 98%). This liquid was analyzed by the measurement of $^1$H-NMR, $^{19}$F-NMR and IR spectra. As a result thereof, the liquid was confirmed to be an amide compound represented by the formula (vi) illustrated below.

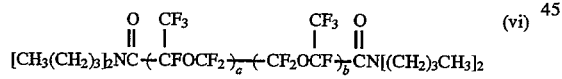

Additionally, the assignment in NMR data set forth below have one to one correspondence to the letters attached to hydrogen and fluorine atoms respectively in the following formula (vii):

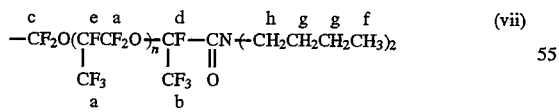

$^1$H-NMR (TMS standard) f: $\delta$=0.83~1.17 (m, 12H); g: $\delta$=1.17~2.00 (m, 16H); h: $\delta$=3.03~3.71 (m, 8H).

$^{19}$F-NMR (CF$_3$COOH standard) a: $\delta$=–3.71 ppm; b: $\delta$=–5.22 ppm; c: $\delta$=–8.99 ppm; d: $\delta$=–46.97 ppm; e: $\delta$=–67.35 ppm.

IR $\nu_{+sc\ C-O}$:1690 cm$^{-1}$; $\nu_{+sc\ C-F}$:1100~1300 cm$^{-1}$.

Further, F$^-$ contamination of the amide compound obtained was determined by ion chromatography. Thus, the F$^-$ content was found to be 15 ppm.

COMPARATIVE EXAMPLE 1

The reaction of the same acylfluoride compound as used in Example 1 with n-butylamine was carried out in the same manner as in Example 1. Unlike Example 1, however, the thus produced reaction mixture in the flask was transferred into a separating funnel without adding diethylaminotrimethylsilane thereto. Then, 200 g of purified water was added to the separating funnel, and shaken. The resulting mixture was allowed to stand for separation. Such a washing operation was repeated 3 times in all. Each washing operation required about 1 hour because the reaction product didn't readily separate from water. The lower layer was isolated from the separating funnel, and distilled. Thus, 18.9 g of the same amide compound of formula (ii) as in Example 1 was obtained (in a yield of 69%). Further, the F$^-$ contamination of the amide compound obtained was determined by ion chromatography. Thus, F$^-$ content was found to be 240 ppm.

What is claimed is:

1. A method of producing an amide compound which comprises adding at least one Si—N bond-containing compound selected from the group consisting of a silazane compound and a silane compound having at least one Si—N bond to a reaction mixture obtained by the reaction of an acylfluoride group-containing compound with an amino compound, the reaction mixture containing the amide compound and hydrogen fluoride or a salt formed by hydrogen fluoride and the amino compound or a mixture of hydrogen fluoride and said salt, to remove the hydrogen fluoride, said salt or the mixture thereof from the reaction mixture.

2. A method of producing an amide compound as described in claim 1, wherein the Si—N bond-containing compound is a silazane compound chosen from the group consisting of tetraorganodisilazanes, hexaorganodisilazanes, heptaorganodisilazanes, hexaorganocyclotrisilazanes and octaorganocyclotetrasilazanes.

3. A method of producing an amide compound as described in claim 1, wherein the Si—N bond-containing compound is a silane compound represented by the following formula (I):

wherein at least one of the substituents $R^1$ to $R^4$ is a group represented by the following formula (II) or (III), and the other substituents are the same or different, each substituent being a hydrogen atom or an unsubstituted or substituted monovalent hydrocarbon group containing 1 to 8 carbon atoms;

wherein $R^5$ and $R^6$ are the same or different, each being a hydrogen atom or an unsubstituted or substituted monovalent hydrocarbon group containing 1 to 8 carbon atoms which may contain one or more of a hetero atom in the carbon chain, and $R^7$ is a substituted or unsubstituted divalent hydrocarbon group containing 2 to 8 carbon atoms which may contain one or more of a hetero atom in the carbon chain.

4. A method of producing an amide compound as described in claim 1, wherein the Si—N bond-containing compound is added in an amount such that the number of Si—N bonds corresponds to 1.0 to 10.0 times as many as the number of the acylfluoride groups present in the reaction mixture.

5. A method of producing an amide compound as described in claim 1, wherein the Si—N bond-containing compound is added to the reaction mixture under a temperature ranging from 0° C. to 80° C.

6. A method of producing an amide compound as described in claim 1, wherein the acylfluoride group-containing compound is a compound chosen from the group consisting of those represented by the following formulae:

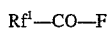

$Rf^1$—CO—F

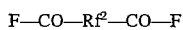

F—CO—$Rf^2$—CO—F

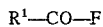

$R^1$—CO—F

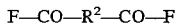

F—CO—$R^2$—CO—F wherein $Rf^1$ is a monovalent perfluoroalkyl group or a monovalent perfluoroalkyl ether group which has at least one oxygen atom forming an ether linkage, $Rf^2$ is a divalent perfluoroalkylene group or a divalent perfluoroalkylene ether group which has at least one oxygen atom forming an ether linkage, $R^1$ is a monovalent hydrocarbon group containing 1 to 20 carbon atoms, and $R^2$ is a divalent hydrocarbon group containing 1 to 20 carbon atoms.

7. A method of producing an amide compound as described in claim 1, wherein the amino compound is ammonia or a compound chosen from the group consisting of primary amino group-containing compounds and secondary amino group-containing compounds.

8. A method of producing an amide compound as described in claim 1, wherein the reaction of an acylfluoride group-containing compound with an amino compound is carried out in the presence of an acid acceptor.

9. A method of producing an anode compound as described in claim 8, wherein the acid acceptor is a tertiary amino compound.

10. The method of claim 1, wherein the amino compound is selected from the group consisting of monoalkylamines, monoalkenylamines, dialkylamines and trialkylamines.

11. The method of claim 1, wherein the hydrogen fluoride, said salt or the mixture thereof are removed by reaction with the Si—N bond-containing compound to prepare fluorosilane and amino compounds which are separated by stripping or distillation.

* * * * *